United States Patent
François et al.

(10) Patent No.: US 6,627,641 B1
(45) Date of Patent: *Sep. 30, 2003

(54) ANTIMALARIAL NAPHTHYLISOQUINOLINE ALKALOIDS AND PHARMACEUTICAL COMPOSITIONS AND MEDICAL USES THEREOF

(75) Inventors: Guido François, Ostend (BE); Gerhard Bringmann, Wurzburg (DE); J. David Phillipson, Sandhurst (GB); Michael R. Boyd, Ijamsville, MD (US); Laurent Aké Assi, Abidjan (ZA), West Africa..JMF; Christoph Schneider, Würzburg (DE); Georges Timperman, Wilrijk (BE)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/843,582

(22) Filed: Apr. 16, 1997

Related U.S. Application Data

(62) Division of application No. 08/195,547, filed on Feb. 14, 1994, now Pat. No. 5,639,761.

(51) Int. Cl.$^7$ .................. A61K 31/472; A61K 31/47; A61P 33/06

(52) U.S. Cl. ............... 514/307; 514/308; 514/309; 546/140; 546/141; 546/146; 546/147; 546/149

(58) Field of Search ................. 546/146, 147, 546/149, 140; 514/307, 308, 309

(56) References Cited

U.S. PATENT DOCUMENTS

| | | | |
|---|---|---|---|
| 3,751,419 A | 8/1973 | Ziegler | 260/288 |
| 4,096,190 A | 6/1978 | Rutledge | 568/730 |
| 5,001,115 A | 3/1991 | Sloan | 514/34 |
| 5,025,020 A | 6/1991 | VanDyke | 514/280 |
| 5,260,315 A | 11/1993 | Bringmann et al. | 514/307 |
| 5,409,938 A | 4/1995 | Boyd et al. | 546/140 |
| 5,455,251 A | 10/1995 | Boyd et al. | 514/307 |
| 5,552,550 A | 9/1996 | Bringmann et al. | 546/146 |
| 5,571,919 A | 11/1996 | Bringmann et al. | 546/146 |
| 5,578,729 A | 11/1996 | Bringmann et al. | 546/140 |
| 5,639,761 A | 6/1997 | Francois et al. | 514/307 |
| 5,654,432 A | 8/1997 | Boyd et al. | 546/140 |

FOREIGN PATENT DOCUMENTS

| | | |
|---|---|---|
| WO | WO 92/18125 | 10/1992 |
| WO | WO 94/24108 | 10/1994 |
| WO | WO 95/21616 | 8/1995 |
| WO | WO 95/21826 | 8/1995 |

OTHER PUBLICATIONS

Bringmann et al., "The determination of the absolute configuration of N–methylated 1,3–dimethyltetrahydroisoquinolines by oxidative degradation," *Planta Med.*, 59 (supp.), A619–A620 (1993).

Bringmann et al., "The absolute configuration of michellamine B, a 'dimeric', anti–HIV–active naphthylisoquinoline alkaloid," *Agnew. Chem.* (*International Edition-English*), 32, 1190–1191 (1993).

Bringmann et al., "Feeding deterrency and growth retarding activity of the naphthylisoquinoline alkaloid dioncophylline A against *spodoptera littoralis*," *Phytochemistry*, 31, 3821–3825 (1992).

Bringmann et al., "Ancistrobrevine B, the first naphthylisoquinoline alkaloid with a 5,8'–coupling site, and related compounds from *ancistrocladus abbreviatus*," *Phytochemsitry*, 31, 4011–4014 (1992).

Bringmann et al., "(±)–Dioncophyllacine A, a naphthylisoquinoline alkaloid with a 4–methoxy substituent from the leaves of *triphyphyllum peltatum*," *Phytochemistry*, 31, 4015–4018 (1992).

Bringmann et al., "Dioncophylline C from the roots of *triphyophyllum peltatum*, the frist 5,1'–coupled dioncophyllaceae alkaloid," *Phytochemistry*, 31, 4019–4024 (1992).

Bringmann et al., "Dioncoline A and its atropisomer: "Inverse hybrid type" ancistrocladaceae/dioncophylliceae alkaloids from *ancistrocladus abbreviatus*," *Planta Med.*, 58, (Supp. 1), A702–A703 (1992).

Bringmann et al., "Isolation, structure elucidation, and total synthesis of ancistrocline, an alkaloid of *ancistrocladus tectorius*," *Planta Med.*, 58, (Suppl. 1), A704 (1992).

Bringmann et al., "Ancistrobrevine D: An unusual alkaloid from *ancistrocladus abbreviatus*," *Planta Med.*, 58, (Supp. 1), A703–A704 (1992).

Bringmann et al., "Atrop–diastereomer separation by racemate resolution techniques: N–methyl–dioncophylline A and its 7–epimer from *ancistrocladus abbreviatus*," *Phytochemistry*, 30, 1307–1310 (1991).

Bringmann et al., "Dioncopeltine A and dioncolactone A: Alkaloids from *triphyophyllum peltatum*," *Phytochemistry*, 30, 1691–1696 (1991).

Bringmann et al., "Dioncophylline B, a naphthylisoquinoline alkaloid with a new coupling type from *triphyophyllum peltatum*," *Phytochemistry*, 30, 3845–3847 (1991).

(List continued on next page.)

Primary Examiner—Evelyn Mei Huang
(74) Attorney, Agent, or Firm—Leydig, Voit & Mayer, Ltd.

(57) ABSTRACT

The present invention provides antimalarial pharmaceutical compositions containing antimalarial naphthylisoquinoline alkaloids or antimalarial derivatives thereof, useful new antimalarial naphthylisoquinoline alkaloid derivatives, methods for obtaining such derivatives, and methods of using such antimalarial compounds for the prevention of malaria infections in mammals and for treating mammals with malarial infections. The antimalarial compounds of the present invention inhibit the reproduction and cytopathicity of Plasmodium sp. parasites in vitro and in vivo.

18 Claims, No Drawings

OTHER PUBLICATIONS

Bringmann et al., "On the biosynthesis of acetogenic tetrahydroisoquinoline alkaloids: first in vivo feeding experiments," *Planta Med.*, 57, (Supp. 2), A98 (1991).
Bringmann et al., "First total synthesis of (−)−dioncophylline A ('triphyophylline') and of selected stereoisomers: complete (revised) stereostructure," *Tetrahedron Lett.*, 31, 643–646 (1990).
Bringmann et al., "On the structure of the dioncophyllaceae alkaloids dioncophylline A ('triphyophylline') and 'O–methyl–triphyophylline'," *Tetrahedron*, 31, 639–642 (1990).
Bringmann et al., "Chiral economy with respect to rotational isomerism: rational synthesis of hamatine and (optionally) ancistrocladine from joint helical precursors," Heterocycles, 28, 137–42 (1989).
Bringmann, "The Naphthyl Isoquinoline Alkaloids," *The Alkaloids*, 29, (brossi, ed.), Chapter 3, 141–184 (Academic Press, New York, 1986).
Bringmann et al., "Regioselective and atropoisometric–selective aryl coupling to give naphthylisoquinoline alkaloids the frist total synthesis of levo ancistrocladine," *Agnew. Chem. (International Edition–English)*, 25, (10), 913–915 (1986).
Bundgarrd, "Design of Prodrugs," Elsevier, Amsterdam, pp. 1–3, 10, 35–36 (1985).
Chen et al., "isolation and identification of the alkaloids from *ancistrocladus tectorius*," *Yao Hsueh Hsueh Pao (China)* (i.e., *Acta pahrmaceutica Sinica*), 16, 519–523 (1981).
Desjardins et al., "Quantitative assessment of antimalarial activity in vitro by a semiautomated microdilution technique," *Antimicrobial Agents Chemother.*, 16, 710–718 (1979).
Ekong et al., "Comparison of the in vitro activities of quassinoids with activity against *plasmodium falciparum*, anisomycin and some other inhibitors of eukaryotic protein synthesis," *Biochem. Pharmacol.*, 40, 297–301 (1990).
Fleischhauer et al., "Messung und Berechnung der CD–Spektron der Biaryl–Alkaloide Ancistrocladein und Dioncophyllein A," *Z. Naturforsch*, 48b, 140–148 (1993).
Foucher et al., *Plantes Med. Pytother.*, 9, 87–98 (1975).
François et al., "Activity of Extracts and Naphthylisoquinoline Alkaloids from *Triphyophyllum peltatum*, *Ancistrocladus abbreviatus* and *A. barteri* against *Plasmodium falciparum* in vitro," *Phytochem.*, 35, 1461–1464 (1994).
Grimm et al., "Deleterious effects of naphthylisoquinoline alkaloids on survival and growth of *spodoptera littoralis*," *Planta Med.*, 58, (Supp. 1), A630 (1992).
Guinaudeau et al., "Bisbenzylisoquinoline alkaloids from *cyclea barbata*," *J. Nat. Prod.*, 56, 1989–1992 (1993).
Hallock et al., "Korupensamines A–D, Novel Antimalarial Alkaloids from *Ancistrocladus korupensis*," *J. Org. Chem.*, 59, 6349–6355 (1994).
Hallock et al., "Preparative Separation of Naphthyltetrahydroisoquinoline Alkaloids from *Ancistrocladus korupensis* by Centrifugal Partition Chromatography," *J. Chromatograph.*, 688, 1–2 (1994).
Likhitwitayawuid et al., "Cyctotoxic and antimalarial bisbenzylisoquinoline alkaloids from *stephania erecta*," *J. Nat. Prod.*, 56, 30–38 (1993).
Lin et al., "Cytotoxic and antimalarial bisbenzylisoquinoline alkaloids from *cyclea barbata*," *J. Nat. Prod.*, 56, 22–29 (1993).
Manfredi et al., "Novel alkaloids from the tropical plant *ancistrocladus abbreviatus* inhibit cell killing by HIV–1 and HIV–2," *J. Med. Chem.*, 34, 3402–3405 (1991).
Merck Index, Ninth Edition p. 276, 1047–1048 (1976).
O'Neill et al., "Plants as sources of antimalarial drugs, Part 1, In vitro test method for the evaluation of crude extracts from plants," *Planta Med.*, 51, 394–399 (1985).
Pavanand et al., "Antimalarial activity of *tiliacora triandr* dields against *plasmodium falciparum* in vitro," *Phytother. Res.*, 3, 215–217 (1989).
Ruangrungsi et al., "Traditional medicinal plants of Thailand, V. ancistrotectorine, a new naphthaleneisoquinoline alkaloid from *ancistroclaus tectorius*," *J. Nat. Prod.*, 48, 529–535 (1985).
Sharma et al., "Alkaloids and terpenoids of *ancistrocladus heyneanus, sgittaria sagitifolia, lyonia formosa* and *hedychium soicatum*," *Phytochemistry*, 14, 578–579 (1975).
Trager et al., "Human malarial parasites in continuous culture," *Science*, 193, 673–675 (1976).
Ye et al., "Selective antimalarial activity of tetrandine against chloroquinone resistant *palsmodium falciparum*," *Biochem. Biophys. Res. Com.*, 159, 242–248 (1989).
Anonymous, "Natural Product Agents in Development by the United States National Cancer Institute (NCI)," *J. Natural Products*, 55(7), 1018–1019 (1992).
Baptistella et al., "1, 8–Diazabicyclo[5.4.0]undec–7–ene as a Mild Deprotective Agent for Acetyl Groups," *Synthesis*, 436–438 (1989).
Benfield et al., "Studies of Fungal and Plant Laccases," *Phytochemistry*, 3, 79–88 (1964).
Berthelot et al., "Bromation Regioselective en Serie Aromatique. I: Monobromation en Position para de Phenols et d'amines Aromatiques par le Tribromure de Tetrabutylammonium," *Can. J. Chem.*, 67, 2061–2066 (1989).
Bobbitt, et al., "Electrochemistry of Natural Products. III. A Stereoselective, Stereospecific Phenol Coupling Reaction," *J. Am. Chem. Soc.*, 93, 3551–3552 (1971).
Boyd et al., *Chemical Abstracts*, 117 (11), Abstract No. 104239k, p. 98 (Sep. 14, 1992).
Boyd et al., "Anti–HIV Michellamines from *Ancistrocladus korupensis*," *J. Medicinal Chemistry*, 37(12), 1740–1745 (1994).
Bringmann et al., "Atropdiastereoselective Ring Opening of Bridged, 'Axial–prostereogenic' Biaryls: Directed Synthesis of (+)– Ancistrocladisine," *Agnew. Chem. Int. Ed. Engl.*, 28 (12), 1672–1673 (1989).
Bringmann et al., "Biomimetic Oxidative Dimerization of Korupensamine A: Completion of the First Total Synthesis of Michellamines A, B, and C," *Tetrahedron*, 50(32), 9643–9648 (1994).
Bringmann et al., "Biomimetische Synthesen beider Molekulhalften der Ancistrocladus– und der Triphyophyllum–Alkaloide aus gemeinsamen Vorstufen," *Liebigs Ann. Chem.*, 2126–2134 (1985).
Bringmann et al., "Circular Dichroism of Michellamines: Independent Assignment of Axial Chirality by Calculated and Experimental CD Spectra," *Tetrahedron*, 50 (26), 7807–7814 (1994).
Bringmann et al., "The Cultivation of Tropical Lianas of the Genus Ancistrocladus," *Planta Med.*, 59 (supp.), A623–624 (1993).

Bringmann et al., "Improved Methods for Dehydration and Hydroxy/Halogen Exchange Using Novel Combinations of Triphenylphosphine and Halogenated Ethanes," *Synthesis*, 139–141 (1983).

Bringmann et al., "Isoquinolines and Naphthalines from β–Polyketones: Model Reactions for an Extraordinary Alkaloid Biosynthesis," *Angew. Chem. Int. Ed. Engl.*, 21(3), 200–201 (1982).

Bringmann et al., "A New Atropisometric Dioncophylline A derivative from *Triphyophyllum peltatum*," *Planta Med.*, 59(supp.), A621–622 (1993).

Bringmann et al., "Stereocontrolled Ring Opening of Axially Prostereogenic Biaryl Lactones with Hydrogen Nucleophiles: Directed Synthesis of a Dioncophylline A Precursor and (Optionally) its Atroodiastereomer," *Synthesis*, 825–827 (1991).

Bringmann et al., "The Synthesis of All Possible Isomeric 6, 8–Dioxygenated 1, 3–Dimethyl–1, 2, 3, 4–tetrahydeoisoquinoline Methyl Ethers—Useful Chiral Building Blocks for Naphthylisoquinoline Alkaloids," *Liebigs Ann. Chem.*, 877–878 (1993).

Casey et al., "Interconversion of γ–Silyl α, β–Unsaturated Carbonyl Compounds and Siloxybutadienes by 1, 5–Shifts of Silicon Between Carbon and Oxygen," *J. Org. Chem.*, 46, 2089–2092 (1981).

Chapman et al., "Synthesis of Triflates of 2, 4–Dinitrophenol and N–Hydroxysuccinimide," *Synthesis*, 591–592 (1971).

Farina et al., "Polycyclic Hydroxyuinones—VIII," *Tetrahedron*, 38 (10), 1531–1527 (1982).

Flaig et al., "Reaktionen Mit Oxodierenden Enzymen Aus Mikroorganismen," *Planta Med.*, 9, 123–139 (1961).

Fleischhauer et al., "Messung und Berechnung der CD–Spektren der Biaryl–Alkaloids Ancistrocladein un Dioncophyllein A," *Z. Naturforsch*, 48b, 140–148 (1993).

Gulakowski et al., "A Semiautomatic Multiparameter Approach for Anti–HIV Drug Screening," *J. Virological Methods*, 33, 87–100 (1991).

Gustafson et al., "AIDS–Antiviral Sulfolipids from Cyanobacteria (Blue–Green Algae)," *J. National Cancer Institute*, 81(16) (Aug. 16, 1989).

Handford et al., "Syntheses of Eleutherolic Acid," *J. Chem. Soc.*, 3896–3897 (1963).

Harel et al., "Purification and Multiplicity of Catechol Oxidase from Apple Chloroplasts," *Phytochemistry*, 4, 783–790 (1965).

Hodgson et al., "The Action of Fuming Nitric Acid on the 4–Halogeno–2: 6–dibromo–phenols and –anisoles. Anomalous Behaviour of Fluorine Derivatives," *J. Chem. Soc.*, 1085–1087 (1930).

Holland, in *Organic Synthesis with Oxidative Enzymes*, Chapter 8, Miscellaneous Oxidative Bioconversions, "1. Oxidative Coupling of Phenols and the Formation of Quinones," VCH, Weinheim, 341–351, 380–381 (1992).

Hoye et al., "Total Synthesis of Michellamines A–C: Important Anti–HIV Agents," *Tetrahedron Letters*, 35 (47), 8747–8750 (1994).

Ismail et al., "Synthesis of Benzothiazoles. α–Amino–(4–hydroxy–6–benzothiazolyl) Propionic Acid," *J. Org. Chem.*, 45, 2243–2246 (1980).

Kelly et al., "Convergent Total Synthesis of the Michellamines," *Tetrahedron Letters*, 35(41), 7621–7624 (1994).

Laatsch, "Isodiospyrin und Elliptinon.—Synthese 6, 6'–dimerer Bijuglone durch Phenoloxidation," *Liebigs Ann. Chem.*, 319–339 (1984).

Laatsch, "Sythese von Biramentaceon, Mamegakinon und Rotundichinon," *Liebigs Ann. Chem.*, 1321–1347 (1980).

Lipshutz et al., "Cyanocuprate–Mediated Intramolecular Biaryl Couplings Applied to an Ellagitannin. Synthesis of (+)–O–Permethyltellimagrandin II," *Tetrahedron*, 35 (31), 5567–5570 (1994).

McMahon et al., "Diarylsulfones, a New Class of Non-nucleoside Antiviral Inhibitors of Human Immunodeficiency Virus Type I Reverse Transcriptase," *Antimicrobial Agents and Chemotherapy*, 37 (4), 754–760 (1993).

Manfredi et al., "Novel Alkaloids from the Tropical Plant *Ancistrocladus Abbreviatus* Inhibit Cell Killing by HIV–1 and HIV–2," *J. Medicinal Chemistry*, 34 (12), 3402–3405 (1991).

Nicholl, in *An Introduction to Genetic Engineering*, Cambridge Univ. Press, Cambridge, pp. 1–5 & 127–130 (1994).

Old et al., in *Principles of Gene Manipulation*, Blackwell Scientific Publishers, London, pp. 3–13 & 108–221 (1992).

Owton et al., "tert–Butyl–3–Carboxyethyl–3–Phosphonodiethylpropionate. A Novel Reagent for Stobbe–like Condensations," *Synthetic Communications*, 23 (15), 2119–2125 (1993).

Pearson et al., "The Ortho Bromination of Phenols," *J. Org. Chem.*, 32, 2358–2360 (1967).

Rizzacasa et al., "The Synthesis of Stypandrol, A Toxic Binaphthalenetetrol Isolated from *Stypandra imbricata*: New Synthesis of Dianellidin and Stypandrone," *Aust. J. Chem.*, 41, 1087–1097 (1988).

Rizzacasa et al., "Synthetic Approaches to the Alkaloids of the Ancistrocladaceae: Dehydroancistrocladisine," *J. Chem. Soc.*, 301–302 (1989).

Robb et al., On the Heterogeneity of the Tyrosinase of Broad Bean (*Vicia Faba L.*), *Phytochemistry*, 4, 731–740 (1965).

Ruangrungsi et al., "Traditional Medicinal Plants of Thailand, V. Ancistrotectorine, A New Naphthalene–Isoquinoline Alkaloid from *Ancistrocladus tectorius*," *J. Natural Products*, 48 (4), 529–535 (Jul.–Aug. 1985).

Sandström et al., "Antiviral Therapy in AIDS Clinical Pharmacological Properties and Therapeutic Experience To Date," *Drugs*, 34, 373–390 (1987).

Saunders, *Peroxidase*, Butterworth, London, pp. 1–52 (1964).

Savard et al., "Reactions of Ketene Acetals—14," *Tetrahedron*, 40 (18), 3455–3464 (1984).

Scott, "Oxidative Coupling of Phenolic Compounds," in *Quarterly Reviews*, (London), 19, 1–35 (1965).

Shimizu et al., "A Simple and Efficient Synthesis of 2–, 3–, or 4– (2–Nitrophenyl) pyridine Derivatives via Palladium Catalyzed Ullmann Cross–Coupling Reaction," *Tetrahedron Letters*, 34 (21), 3421–3424 (1993).

Snieckus, "Directed Ortho Metalation. Tertiary Amide and O– Carbamate Directors in Synthetic Strategies for Polysubstituted Aromatics," *Chemical Reviews*, 90, 879–933 (1990).

Sofer, *Introduction to Genetic Engineering*, Butterworth-Heinemann, Stoneham, MA, pp. 1–21 & 103–126 (1991).

Steinberg et al., in *Recombinant DNA Technology Concepts and Biomedical Applications*, Prentice Hall, Englewood Cliffs, NJ, pp. 81–124 & 150–162 (1993).

Stuart–Harris et al., in *The Background to Chemotherapy of Virus Diseases*, Chapter 5, 76–77 (Charles C. Thomas Publishers, Springfield, IL, 1965).

Supko et al., "Determination of Michellamine B in Biological Fluids by High–Performance Liquid Chromatograph with Flourescence Detection," *Analytical Biochemistry, 216*, 52–60 (1994).

Suzuki, "New Synthetic Transformations via Organoboron Compounds," *Pure & Appl. Chem., 66* (2), 213–222 (1994).

Thomas et al., "*Ancistrocladus korupensis* (Ancistrocladaceae): A New Specis of Liana from Cameroon," *Novon, 3*(4), 494–498 (1993).

Vilietstra et al., "Trimethylacetic Formic Anhydride. Improved Preparation and Use As a Highly Efficient and Selective N–formylating Reagent," *J. Royal Netherlands Chemical Society, 101*, 460–462 (1982).

Watanabe et al., "Synthesis of Sterically Hindered Biaryls via the Palladium–Catalyzed Cross–Coupling Reaction of Arylboronic Acids or their Esters with Haloarenes," *Synlett*, 207–210 (Mar. 1992).

Weislow et al., "New Soluble–Formazan Assay for HIV–1 Cytopathic Effects: Application to High–Flux Screening of Synthetic and Natural Products for AIDS–Antiviral Activity," *J. National Cancer Institute, 81* (8), 577–586 (Apr. 19, 1989).

Whiting, in *Comprehensive Organic Synthesis*, (Trost and Fleming, eds.), Peragamon Press, Oxford, 659–703 (1991).

ANTIMALARIAL NAPHTHYLISOQUINOLINE ALKALOIDS AND PHARMACEUTICAL COMPOSITIONS AND MEDICAL USES THEREOF

This is a divisional of application(s) Ser. No. 08/195,547, filed on Feb. 14, 1994, now U.S. Pat. No. 5,639,761.

TECHNICAL FIELD OF THE INVENTION

The present invention relates to naphthylisoquinoline alkaloids and derivatives thereof which exhibit in vitro and in vivo antimalarial activity, methods of obtaining useful antimalarial naphthylisoquinoline derivatives, pharmaceutical compositions containing such antimalarial compounds, and methods for using the compounds for the treatment or prevention of malaria. The compounds of the present invention exhibit advantageous pharmacological, toxicological, or antimalarial properties, such as for example, inhibiting in vitro and in vivo the viability, growth, reproduction, and pathological effects of Plasmodia parasites, including drug-resistant strains thereof, which are known to cause malaria.

BACKGROUND OF THE INVENTION

It is estimated that more than 2–3 million people die of malaria each year, and many more suffer from debilitating infection. Approximately a third of the world's population lives in malaria-endemic areas, including Central and South America, Asia, and Africa. Transient visitors or workers in these areas also are at ever-increasing risk of contracting malaria. Mosquitoes that carry malaria parasites have become resistant to insecticides, and the deadliest parasites have become resistant to previously effective antimalarial drugs such as chloroquine and other clinically used agents. New effective antimalarial chemotherapy agents are urgently needed. The present invention provides useful new antimalarial compounds and pharmaceutical compositions, as well as methods of using such antimalarial compounds and pharmaceutical compositions to prevent or treat malaria. These and other objects and advantages of the present invention, as well as additional inventive features, will be apparent from the description of the invention provided herein.

BRIEF SUMMARY OF THE INVENTION

The present invention is directed to useful antimalarial pharmaceutical compositions comprised of a suitable, pharmaceutically acceptable carrier and an antimalarial effective amount of at least one naphthylisoquinoline alkaloid selected from the group consisting of dioncophylline B, dioncopeltine A, dioncophylline A, dioncophylline C, dioncolactone A, N-methyl-dioncophylline A, ancistrobrevine D, ancistrocladine, michellamine A, michellamine B, N-methyl-dioncophylline A and atropisomer thereof, 5'-O-demethyl-8-O-methyl-7-epi-dioncophylline A, 4'-O-demethyl-dioncophylline A, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and derivatives thereof wherein one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, or alkyl quaternary ammonium salt; one or more tertiary amine site(s) may instead be a secondary amine; and one or more aromatic hydrogen substituent(s) may instead be a halogen, nitro, amino, hydroxyl, thiol, or cyano substituent, or a pharmacologically acceptable salt thereof.

The present invention additionally includes a method of obtaining useful antimalarial compounds by applying one or more well-known chemical reactions to a naphthylisoquinoline alkaloid selected from the group consisting of dioncophylline B, dioncopeltine A, dioncophylline A, dioncophylline C, dioncolactone A, N-methyl-dioncophylline A, ancistrobrevine D, ancistrocladine, michellamine A, michellamine B, N-methyl-dioncophylline A and atropisomer thereof, 5'-O-demethyl-8-O-methyl-7-epi-dioncophylline A, 4'-O-demethyl-dioncophylline A, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, to provide a naphthylisoquinoline derivative wherein one or more phenolic hydroxyl group(s) may instead be replaced by an ester, sulfonate ester, or ether group; one or more methyl ether group(s) may instead be replaced by a phenolic hydroxyl group; one or more phenolic hydroxyl group(s) may instead be replaced by an aromatic hydrogen substituent; one or more secondary amine site(s) may instead be replaced by an amide, sulfonamide, tertiary amine, or alkyl quaternary ammonium salt; one or more tertiary amine site(s) may instead be replaced by a secondary amine; and one or more aromatic hydrogen substituent(s) may instead be replaced by a halogen, nitro, amino, hydroxyl, thiol, or cyano substituent.

The present invention also encompasses a method of treating or preventing a malaria infection which comprises administering to a mammal in need thereof an antimalarial effective amount of at least one compound selected from the group, consisting of dioncophylline B, dioncopeltine A, dioncophylline A, dioncophylline C, dioncolactone A, N-methyl-dioncophylline A, ancistrobrevine D, ancistrocladine, michellamine A, michellamine B, N-methyl-dioncophylline A and atropisomer thereof, 5'-O-demethyl-8-O-methyl-7-epi-dioncophylline A, 4'-O-demethyl-dioncophylline A, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and derivatives thereof wherein one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, or alkyl quaternary ammonium salt; one or more tertiary amine site(s) may instead be a secondary amine; and one or more aromatic hydrogen substituent(s) may instead be a halogen, nitro, amino, hydroxyl, thiol, or cyano substituent, or a pharmacologically acceptable salt thereof.

The treatment method of the present invention may also involve co-administering an antimalarial effective amount of chloroquine or other antimalarial agent(s), such as mefloquine, halofantrine, artemisinin, artemether, or quinine, with at least one compound, or pharmacologically acceptable salt thereof, selected from the aforementioned antimalarial naphthylisoquinoline alkaloids or derivatives.

DESCRIPTION OF THE PREFERRED EMBODIMENTS

The present invention is predicated on the discovery that certain naphthylisoquinoline alkaloids and derivatives thereof, preferably in substantially pure form, have in vitro and in vivo antimalarial activity, and therefore are useful for antimalarial treatments. Many of these naphthylisoquinoline compounds have chemical formulae, or are derivatives thereof, which have been previously reported in the chemical literature (see Table 1); however, prior to the present invention, none of these compounds were previously known to have in vitro and in vivo antimalarial properties.

TABLE 1

Literature references reporting the isolation and chemical structures of naphthylisoquinoline alkaloids.

| Compound Name | Reference Citation |
|---|---|
| Dioncophylline B | Bringmann et al., Phytochemistry, 30, 3845–3847, 1991 |
| Dioncopeltine A | Bringmann et al., Phytochemistry, 30, 1691–1696, 1991 |
| Dioncophylline A | Bringmann et al., Tetrahedron Lett., 31, 639–642, 1990<br>Bringmann et al., Tetrahedron Lett., 31, 643–646, 1990 |
| Dioncophylline C | Bringmann et al., Phytochemistry, 31, 4019–4024, 1992 |
| Dioncolactone A | Bringmann et al., Phytochemistry, 30, 1691–1696, 1991 |
| N-methyl-dioncophylline A | Bringmann et al., Phytochemistry, 30, 1307–1310, 1991 |
| Ancistrobrevine D | Bringmann et al., Planta Med., 58 (suppl 1), 703–704, 1992 |
| Ancistrocladine | Bringmann, The Alkaloids, 29, 141–184, 1986 (and literature cited therein) |
| Michellamine A | Boyd et al., U.S. patent application Ser. No. 07/684,197 and 08/049,824 and PCT/US93/03682 |
| Michellamine B | Boyd et al., supra; Bringmann et al., Angew Chem., 105, 1242–1243, 1993 |
| N-methyl-dioncophylline A (atropisomers) | Bringmann et al., Phytochemistry, 30, 1307–1310, 1991<br>Bringmann et al., Phytochemistry, submitted, 1993 |
| Dioncophylline A/4'-O-demethyl-dioncophylline A | Bringmann et al., Planta Med., in press, 1993 |
| Dioncophylleine A | Fleischhauer et al., Z. Naturforsch, 48b, 140–148, 1993 |
| (±)-dioncophyllacine A | Bringmann et al., Phytochemistry, 31, 4015–4018, 1992 |

TABLE 1-continued

Literature references reporting the isolation and chemical structures of naphthylisoquinoline alkaloids.

| Compound Name | Reference Citation |
|---|---|
| Hamatine | Bringmann et al., The Alkaloids, 29, 141–184, 1986<br>Bringmann et al., Angew Chem., 98, 917, 1986<br>Bringmann et al., Heterocycles, 28, 137, 1989 (and literature cited therein) |
| Ancistrobrevine B | Bringmann et al., Phytochemistry, 31, 4011–4014, 1992 |
| Ancistrobrevine A | Bringmann et al., Planta Med., 58 (suppl 1), 702–703, 1992 |
| 6-O-demethyl-ancistrobrevine A | (unpublished) |
| Ancistrobarterine A (6-O-demethyl-8-O-methyl-7-epi-ancistrobrevine C) | Bringmann et al., Planta Med., in press, 1993 |
| 7-epi-dioncophylline A | Bringmann et al., Tetrahedron Lett., 31, 643–646, 1990 |
| N-formyl-ancistrocladine | Bringmann et al., Phytochemistry, 31, 4019–4024, 1992 (and literature cited therein) |
| N-methyl-ancistrocladine | Bringmann, The Alkaloids, 29, 141–184, 1986; Bringmann et al., Phytochemistry, 31, 4019–4024, 1992 (and literature cited therein) |
| 6-deoxy-N-methyl-ancistrocladine | Bringmann et al., Phytochemistry, 31, 4019–4024, 1992 |
| N-formyl-O,O-dimethyl dioncophylline C | Bringmann et al., Phytochemistry, 31, 4019–4024, 1992 |
| N-formyl-dioncophylline C | Bringmann et al., Phytochemistry, 31, 4019–4024, 1992 |

The general chemical class of compounds known as naphthylisoquinoline alkaloids are known to occur in plant species of the Ancistrocladaceae and Dioncophyllaceae (see, e.g., Bringmann, The Naphthylisoquinoline Alkaloids, in *The Alkaloids*, Vol. 29, Brossi, ed., Academic Press, New York, 1986, pp. 141–184). These small plant families occur in tropical Africa and southern and southeast Asia. However, prior to the present invention, no known pure compounds of the naphthylisoquinoline alkaloid class have been known specifically to have in vitro and in vivo antimalarial properties or antimalarial uses.

An arguably somewhat related class of naturally occurring compounds, called bisbenzylisoquinoline alkaloids, has been described, and reportedly has in vitro antimalarial activity (Pavanand, et al., *Phytother. Res.*, 3, 215–217, 1989; Ye and VanDyke, *Biochem. Biophys Res. Commun.*, 159, 242–247, 1989; VanDyke, U.S. Pat. No. 5,025,020, 1991; Lin, et al., *J. Nat. Prod.*, 56, 22–29, 1993; Likhitwitayawuid, et al., *J. Nat. Prod.*, 56, 30–38, 1993; Guinaudeau, et al., *J. Nat. Prod.*, 56, 1989–1992, 1993). However, the latter class is distinctly different from the naphthylisoquinoline alkaloid class of the present invention. Moreover, no in vivo antimalarial activity of the bisbenzylalkaloid class is known; in fact it has been concluded by some authors (e.g., Likhitwitayawuid, et al., supra) that "bisbenzylisoquinoline alkaloids do not appear to be promising candidates as antimalarial agents."

The naphthylisoquinoline alkaloids are chemically unique in several respects. Their basic structure comprises a biaryl system consisting of a naphthalene and a isoquinoline or dihydrogenated or tetrahydrogenated isoquinoline moiety with an unprecedented methyl group at C-3. Moreover, many of these alkaloids display atropisomerism due to the bulky ortho-substituents adjacent to the biaryl axis (Bringmann, supra). Such highly unusual structures presumably result from an unprecedented biogenetic origin, for which a polyketide pathway has been implicated (Bringmann, supra; Bringmann, et al., *Planta Med.*, 57, suppl. 2, 98–104, 1991).

Some naphthylisoquinoline alkaloids in their pure forms have been reported to have interesting biological activities: ancistrocladidine (from *A. heyneanus*) had pronounced spasmolytic activity (Sharma, et al., *Phytochemistry*, 14, 578–583, 1975), and ancistrotectorine (from *A. tectorius*) had antitumor activity (Ruangrungsi, et al., supra). Dioncophyllines A and B were active as fungicides (Bringmann, et al., DE 41 17 080), and dioncophylline A had an antifeedant effect against the larvae of Spodoptera littoralis (Grimm, et al., *Planta Med.*, 58, Suppl. 1, 630, 1992; Bringmann, et al., *Phytochemistry*, 31, 3821–3825, 1992). However, prior to the present invention, no pure naphthylisoquinoline alkaloid, nor specific pharmaceutical composition thereof, had ever been shown to have in vitro and in vivo antimalarial activity nor to be useful for treatment or prevention of malaria.

Several species from the Ancistrocladaceae and Dioncophyllaceae have been known to be used in the form of crude plant or extract preparations in folk medicine for treatments of malaria. For example, the roots of Ancistrocladus tectorius reportedly have been used for the treatment of malaria and dysentery (Bringmann, et al., *Tetrahedron Letters*, 31, 639–642, 1990), while other plants, such as *Triphyophyllum peltatum*, reportedly have been used to treat malaria and elephantiasis (see, e.g., Ruangrungsi, et al., *J. Nat. Prod.*, 48, 529–535, 1985). However, pure antimalarial compounds from such crude plant materials have not heretofore been defined, nor provided specifically in pharmaceutical compositions.

The isolation and chemical identification of pure naphthylisoquinoline alkaloids, including ancistrocladine (Foucher, et al., *Plantes Med. Phytother.*, 9, 26–29, 1975), ancistrocladine, hamatine, ancistrocline (Chen, et al., *Yaoxue Xuebaq*, 16, 519–521, 1981; Bringmann, et al., *Planta Med.*, 58 (Suppl. 1), 703–704, 1992), and ancistrotectorine (Ruangrungsi, et al., supra), have been reported from the stems, twigs, or leaves of *Ancistrocladus tectorius*. However, none of these compounds were known to have antimalarial activity, nor were they linked specifically to any antimalarial activity that (presumably) resided in these plants, or extracts therefrom.

Accordingly, the present invention provides antimalarial pharmaceutical compositions comprised of a suitable, pharmaceutically acceptable carrier and an antimalarial effective amount of at least one naphthylisoquinoline selected from the group consisting of dioncophylline B, dioncopeltine A, dioncophylline A, dioncophylline C, dioncolactone A, N-methyl-dioncophylline A, ancistrobrevine D, ancistrocladine, michellamine A, michellamine B, N-methyl-dioncophylline A and atropisomer thereof, 5'-O-demethyl-8-O-methyl-7-epi-dioncophylline A, 4'-O-demethyl-dioncophylline A, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and derivatives thereof wherein one or more phenolic hydroxyl group(s) may instead be an ester, sulfonate ester, or ether group; one or more methyl ether group(s) may instead be a phenolic hydroxyl group; one or more phenolic hydroxyl group(s) may instead be an aromatic hydrogen substituent; one or more secondary amine site(s) may instead be an amide, sulfonamide, tertiary amine, or alkyl quaternary salt; one or more tertiary amine site(s) may instead be a secondary amine; and one or more aromatic hydrogen substituent(s) may instead be a halogen, nitro, amino, hydrokyl, thiol, or cyano substituent, or a pharmacologically acceptable salt thereof (i.e., of the naphthylisoquinoline alkloids or derivatives thereof).

The present inventive compositions may include other active or inactive components. In particular, they may include other antimalarial agents such as an antimalarial effective amount of chloroquine, mefloquine, halofantrine, artemisinin, artemether, pyrimethamine, quinine, or other antimalarial agent.

Certain chemical modification(s) can be introduced as desired into a given naphthylisoquinoline compound to obtain a new derivative with modified biological properties such as: greater antimalarial potency against a particular Plasmodium sp., a broader spectrum of antimalarial activity against diverse Plasmodia sp., enhanced oral bioavailability, less toxicity in a particular host mammal, more advantageous pharmacokinetics and/or tissue distribution in a given host mammal, and the like. Therefore, the present invention additionally provides methods for obtaining such derivatives by applying one or more well-known chemical reactions to a given naphthylisoquinoline alkaloid selected from the group consisting of dioncophylline B, dioncopeltine A, dioncophylline A, dioncophylline C, dioncolactone A, N-methyl-dioncophylline -A, ancistrobrevine D, ancistrocladine, michellamine A, michellamine B, N-methyl-dioncophylline A and atropisomer thereof, 5'-O-demethyl-8-O-methyl-7-epi-dioncophylline A, 4'-O-demethyl-dioncophylline A, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, to provide a derivative wherein one or more phenolic hydroxyl group(s) may instead be replaced by an ester, sulfonate ester, or ether group; one or more methyl ether group(s) may instead be replaced by a phenolic hydroxyl group; one or more phenolic hydroxyl group(s) may instead be replaced be an aromatic hydrogen substituent; one or more secondary amine site(s) may instead be replaced by an amide, sulfonamide, tertiary amine, or alkyl quaternary ammonium salt; one or more tertiary amine site(s) may instead by replaced by a secondary amine; and one or more aromatic hydrogen substituent(s) may instead be replaced by a halogen, nitro, amino, hydroxyl, thiol, or cyano substituent.

The naphthylisoquinoline alkaloids and derivatives, as well as the salts thereof, of the present invention can be used for a variety of in vitro purposes, particularly in assays and the like. These compounds can also be used for in vivo purposes, particularly to prevent and/or treat malarial infections.

The present inventive method of treating or preventing a malarial infection comprises administering to a mammal in need thereof an antimalarial effective amount of at least one of the aforementioned naphthylisoquinoline alkaloids or derivatives thereof, or a pharmacologically acceptable salt thereof (i.e., of the naphthylisoquinoline alkaloids or derivatives thereof). The treatment method may involve the use of the aforementioned antimalarial compositions, and, thus, the treatment method may involve the use of pharmaceutically acceptable carriers and the coadministration of other active or inactive components, in particular, other antimalarial agents such as an antimalarial effective amount of chloroquine, mefloquine, halofantrine, artemisinin, artemether, pyrimethamine, quinine, or other antimalarial agent. The particular infecting malaria-causing organism may be any responsible pathogenic parasite, particularly such as a Plasmodium sp., more :particularly such as *P. falciparum*, *P. vivax*, *P. malariae*, *P. ovale*, or *P. berghei*.

Definitions

The pharmacologically acceptable salt may be any such suitable salt. Examples of pharmacologically acceptable salts include HBr, HCl, oxalate, citrate, acetate, tartrate, and the like.

By $C_1$–$C_6$ alkyl is meant straight or branched-chain $C_1$–$C_6$ alkyl groups. Examples include, but are not limited to, methyl, ethyl, n-propyl, iso-propyl, n-butyl, iso-butyl, sec-butyl, tertiary-butyl, n-pentyl, iso-pentyl, and n-hexyl.

By aryl is meant an organic radical derived from an aromatic hydrocarbon. Examples of an aryl group include phenyl, and o-, m-, and p-hydroxyphenyl.

By aliphatic is meant an organic radical derived from an open hydrocarbon chain. Examples of aliphatic radicals include alkanes, alkenes, and alkynes. Specific examples of aliphatic radicals which can be used in the present invention include, but are not limited to, $C_1$–$C_6$ alkyl radicals, straight or branched.

Structures

The aforementioned naphthylisoquinoline alkaloids which may be employed in the present invention have the following structures:

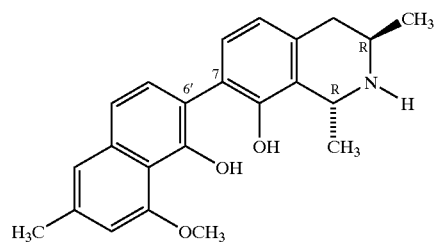

Dioncophylline B

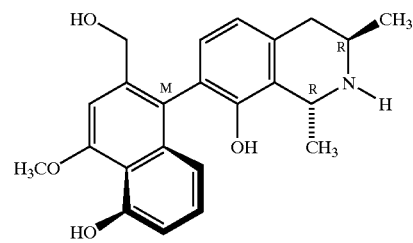

Dioncopeltine A

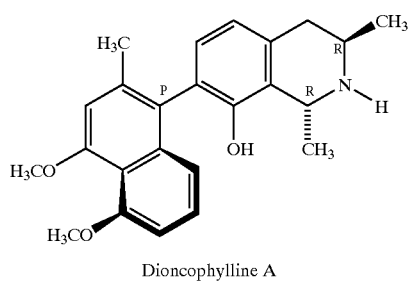

Dioncophylline A

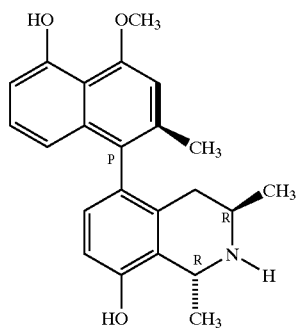

Dioncophylline C

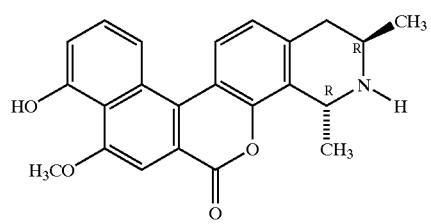

Dioncolactone A

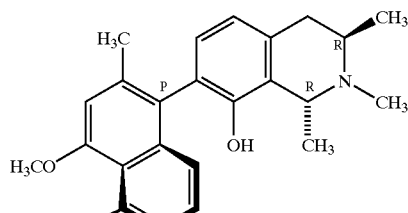

N-Methyl-dioncophylline A

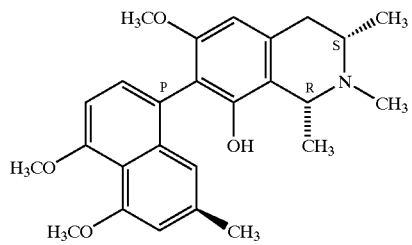

Ancistrobrevine D

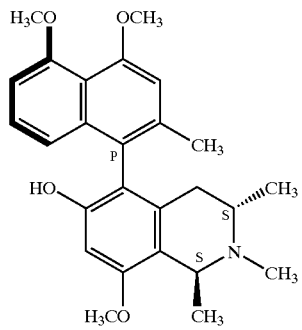
Ancistrocladine
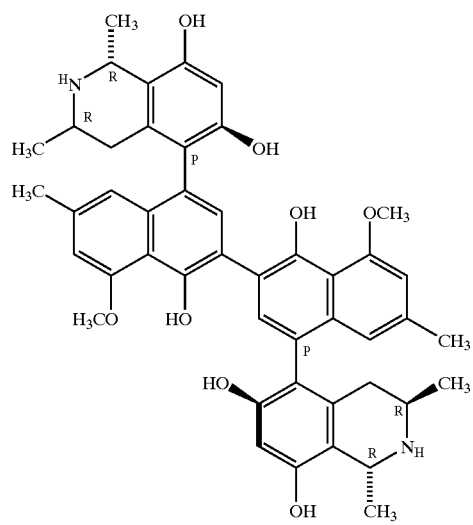
Michellamine A
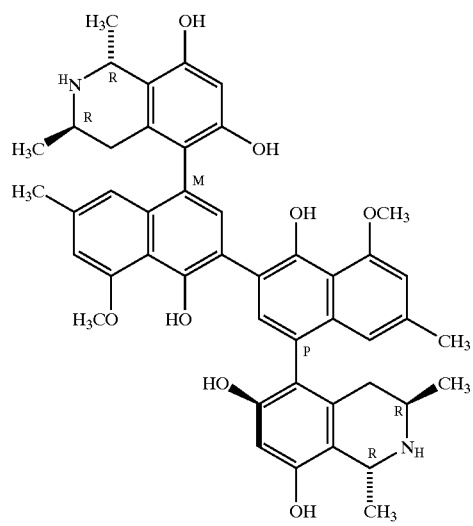
Michellamine B
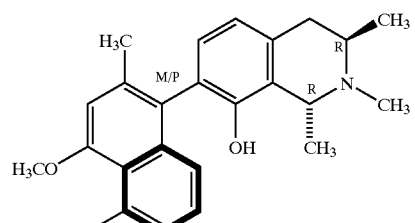
N-Methyl-dioncophylline A
+ Atropoisomer
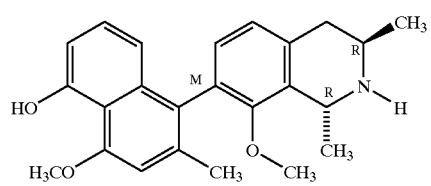
5′-O-Demethyl-8-O-methyl-
7-epi-dioncophylline A
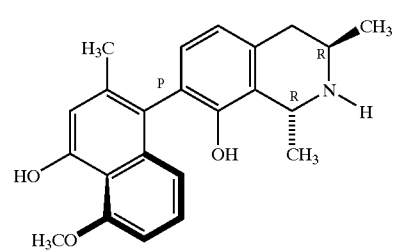
4′-O-Demethyl-dioncophylline A
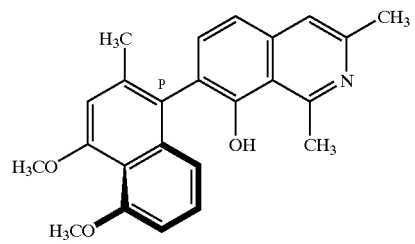
Dioncophylleine A
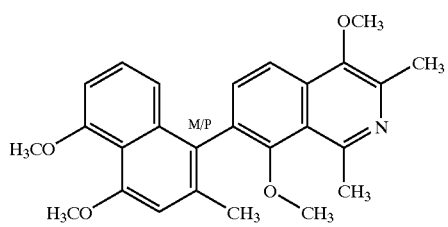
(±)-Dioncophyllacine A -continued
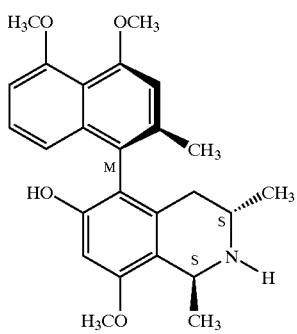
Hamatine
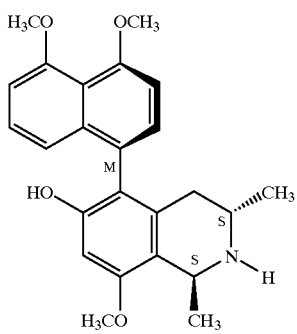
Ancistrobrevine B
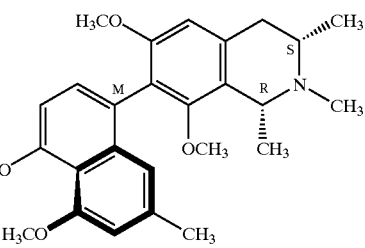
Ancistrobrevine A
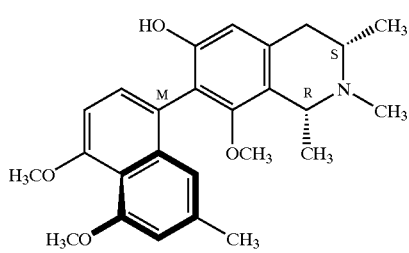
6-O-Demethyl-ancistrobrevine A
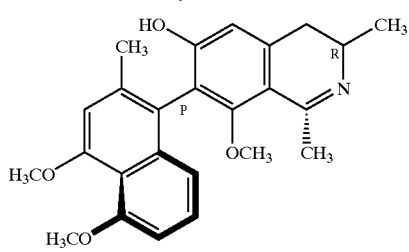
Ancistrobarterine A
(6-O-Demethyl-8-O-methyl-
7-epi-ancistrobrevine C)
-continued
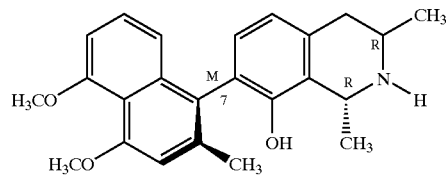
7-epi-Dioncophylline A
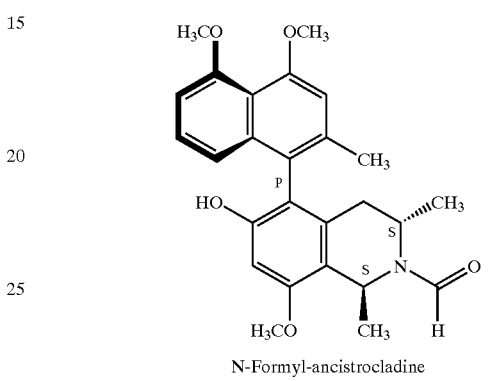
N-Formyl-ancistrocladine
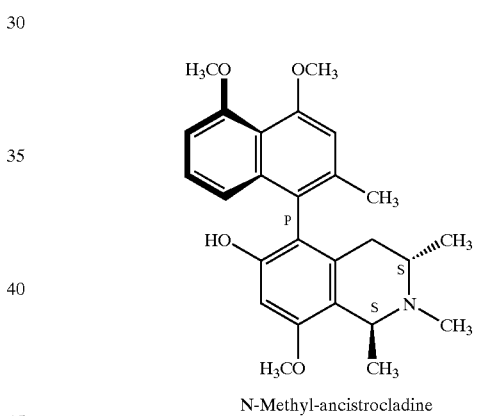
N-Methyl-ancistrocladine
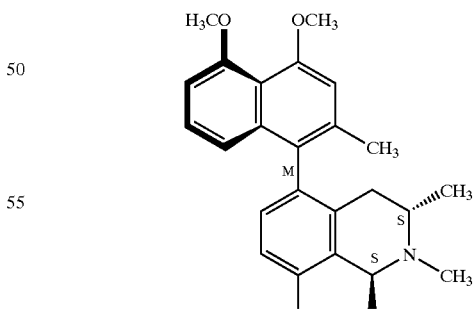
6-Deoxy-
N-Methyl-ancistrocladine

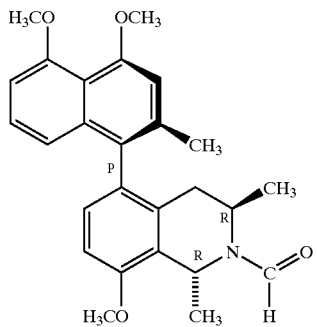
N-Formyl-O,O-dimethyl-
dioncophylline C
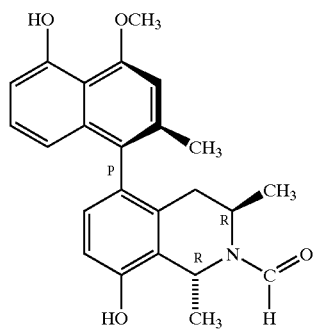
N-Formyl-dioncophylline C
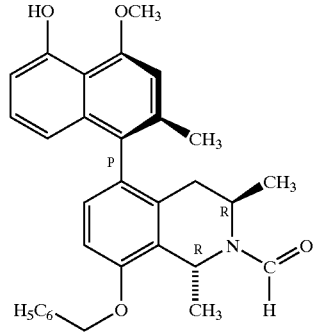
N-Formyl-8-O-benzyl-
dioncophylline C
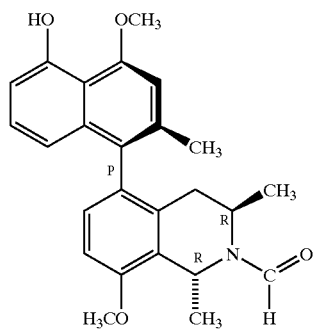
N-Formyl-8-O-methyl-
dioncophylline C
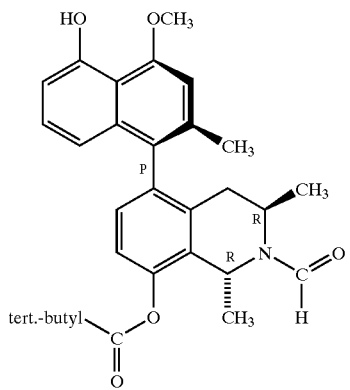
N-Formyl-8-O-pivaloyl-
dioncophylline C
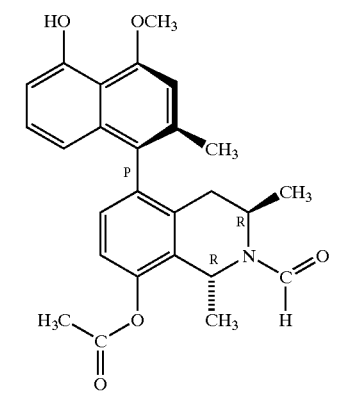
N-Formyl-8-O-acetyl-
dioncophylline C
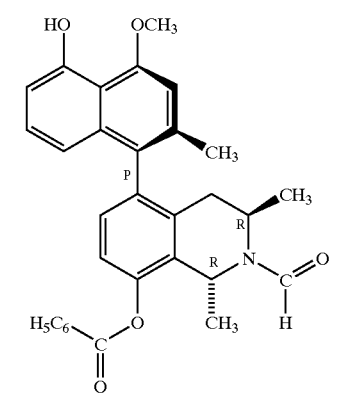
N-Formyl-8-O-benzoyl-
dioncophylline C -continued

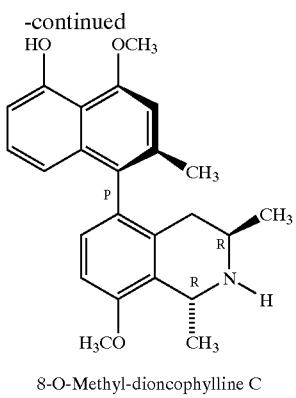

8-O-Methyl-dioncophylline C

EXAMPLES

The following examples further illustrate the present invention, but, of course, should not be construed as in any way limiting its scope.

Example 1

This example illustrates methods for the preparation of useful new antimalarial derivatives of the aforementioned antimalarial naphthylisoquinoline alkaloids. The antimalarial properties of these derivatives can be demonstrated in vitro and in vivo according to the methods shown in Example 2.

Using standard organic chemical methodology, one or more structural modifications of the aforementioned naphthylisoquinoline alkaloids can be made to provide derivatives with modified biological properties which may be advantageously useful for treatment of certain host mammal species and/or against certain parasite strains. Such properties may, for example, include one or more of the following: greater antimalarial potency, broader spectrum of antimalarial activity, enhanced oral bioavailability, less host toxicity, more advantageous pharmacokinetics and/or tissue distribution.

Depending on the stoichiometric amount of the particular reactant, the naphthylisoquinoline compound can be substituted at one, some, or all of the respective available positions. For example, when such a compound is reacted with a certain amount of $CH_3COCl$, acetate can be introduced at one, some, or all the available OH or NH positions.

Examples of these include, but are not limited to:

1. Conversion to ester, sulfonate ester, and ether substituents at one or more phenolic hydroxyl positions in the naphthylisoquinoline compound.

For example, for preparation of esters or sulfonate esters, the selected naphthylisoquinoline compound can be reacted with an acid halide (RCOX or $RSO_2X$, where X=Cl, Br, or I, and R is an $C_1$–$C_6$ aliphatic or aromatic radical) in anhydrous pyridine or triethylamine. Alternatively, the selected compound may be reacted with an acid ($RCO_2H$ or $RSO_3H$ wherein R is an aliphatic or aromatic radical) and dicyclohexylcarbodiimide in triethylamine to prepare the ester or sulfonate ester.

For preparation of ethers, the selected naphthylisoquinoline compound is reacted with an organic halide (e.g., RX or $RCH_2$-X, where X=Cl, Br, or I, and R is a $C_1$–$C_6$ aliphatic or aromatic radical) in anhydrous acetone with anhydrous potassium carbonate.

For instance:

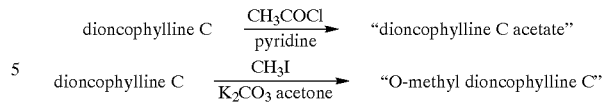

2. Removal of a ether methyl group(s) to provide a phenolic hydroxyl functionality and/or conversion of that moiety to an ester, sulfonate, or other ether:

For example, for hydrolytic cleavage of the methyl ether and conversion to phenolic hydroxyl, the selected naphthylisoquinoline compound is reacted with $BBr_3$ or $BX_3 \cdot (CH_3)_2S$ in $CH_2Cl_2$ (where X=F, Cl, or Br). The resulting phenol can be converted to esters, sulfonate esters, or ethers as described above.

For instance:

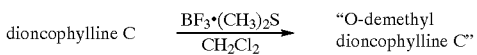

3. Preparation of amide or sulfonamide derivatives at the amine site in a selected naphthylisoquinoline compound:

For example, for preparation of amide or sulfonamide derivatives, the same general procedures described above (in procedure 1) apply. In either case (procedure 1 or 3), an appropriate functional group protection strategy (blocking/deblocking of selected groups) is applied.

For instance:

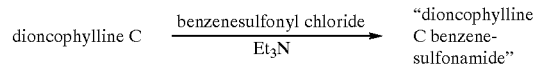

4. Conversion of the secondary amine functionality to an alkyl quaternary ammonium salt or to a tertiary amine:

For example, for preparation of tertiary amines, the selected naphthylisoquinoline alkaloid is reacted with an aldehyde and the resulting product reduced with $NaBH_4$. Alternatively, for preparation of an alkyl ammonium salt, the selected naphthylisoquinoline alkaloid is reacted with an alkyl halide (RX, where X=Cl, Br, or I, and R is an $C_1$–$C_6$ aliphatic radical) in anhydrous aprotic solvent.

For instance:

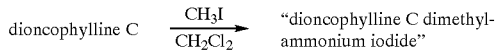

5. Conversion of the tertiary amine function to a secondary amine:

For example, for preparation of a secondary amine, a selected N-alkyl naphthylisoquinoline compound is reacted with cyanogen bromide to give the corresponding cyanamide, which is then treated with $LiAlH_4$.

For instance:

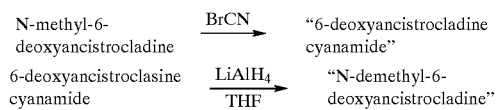

6. Conversion of one or more phenolic hydroxyl groups to an aromatic hydrogen substituent:

For example, the selected naphthylisoquinoline compound is converted (after suitable protection of the amine function if necessary) to the triflic ester, followed by reductive deoxygenation of the triflic ester to give the corresponding 6-deoxykorupensamine.

For instance:

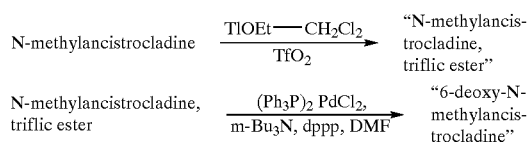

7. Substitution of one or more hydrogen substituents on the aryl systems by halogen, nitro, amino, hydroxyl, thiol, or cyano groups:

For example, for preparation of bromine-substituted derivatives, the selected naphthylisoquinoline compound is reacted with $Br_2$ in $H_2O$. For preparation of other substituted derivatives, the selected naphthylisoquinoline compound is treated with $HNO_3/HOAc$ to provide nitro-substituted ($—NO_2$) derivatives. In turn, the nitro derivative can be reduced to the amino derivative. The amino-derivative is the point of origin of the chloro, iodo, cyano, thiol, and hydroxyl substitution via well-known and practiced diazonium substitution reactions.

For instance:

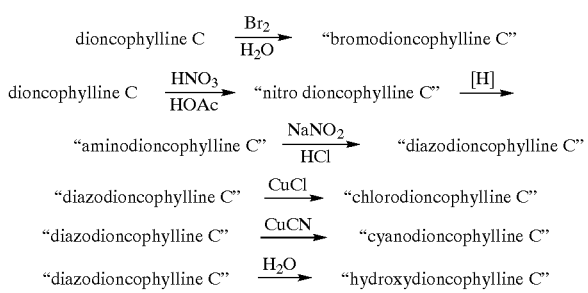

Example 2

This example illustrates the antimalarial activity of the naphthylisoquinoline alkaloids and derivatives of the present invention. The antimalarial activity may be demonstrated both by in vitro as well as in vivo tests, as exemplified in the following.

Continuous in vitro cultures of asexual erythrocytic stages of P. falciparum (strain NF 54/64, clone A1A9) were maintained following essentially the method of Trager and Jensen (Science, 193, 673–675, 1976) at 37° C. under an atmosphere of 5% $CO_2$, 5% $O_2$, and 90% $N_2$. The host cells were human erythrocytes (A or O Rh+). The culture medium was RPMI 1640 (Gibco), containing HEPES (BDH; 4.57 $gL^{-1}$), glucose (Sigma; 1.54 $gL^{-1}$), 5% $NaHCO_3$ (Merck; 34.78 $mlL^{-1}$), and gentamycin (Merck; 8.70 $mlL^{-1}$) supplemented with 10% human plasma (A Rh+). Parasites were subinoculated every 3–4 days with initial conditions of 1% parasitemia and 1% hematocrit.

In vitro testing with P. falciparum was as follows. Each compound was dissolved in DMSO at a concentration of 20 mg $ml^{-1}$. These solutions were further diluted with physiological saline to obtain a stock solution of 500 μg $ml^{-1}$. Each test substance was applied in a series of seven, 4-fold dilutions (maximum concentrations 50 or 5 μg $ml^{-1}$). Each compound was tested in 6-fold repeats. Chloroquine was tested similarly, as a positive control.

The test protocol was performed in vitro, based upon the method of Desjardins, et al. (Antimicrobial Agents Chemother., 16, 710–715, 1979). The parasites (200 μl of a suspension with initial parasitemia of 0.5% and hematocrit of 1.5%) were incubated for 24 h in microtitre plates (Falcon MicroTest III) in hypoxanthine-free medium in the presence of 25 μl of test solution. The plates contained a negative control (6 wells with non-parasitized RBC's, no drug) and a positive control (6 wells with parasitized RBC's no drug). Thereafter, 25 μl of $^3$H-hypoxanthine solution (Amersham) was added (0.5 μCi well $^{-1}$), and the parasites were incubated for a further period of 18 h. Each well was harvested with a Cell Harvester (Nunc). The filter papers were dried for 2 h at 52° C., and their radioactivity was measured by liquid scintillation counting in Optiscint HiSafe (LKB Pharmacia).

The mean results, obtained as counts per min (cpm), were expressed as percentages of incorporation or growth inhibition. The sigmoid dose-response curve was then linearized by probit analysis with the aid of software provided by IWONL (Gent), adapted by G. Timperman and used to derive the $IC_{50}$ values.

For experiments with P. berghei (Anka strain), the parasites were maintained, and the in vitro tests performed essentially the same as above, except for the following modification. In the case of tests using P. berghei, the parasites were incubated in the same conditions as for P. falciparum (above) except that the incubations were started immediately in the presence of the $^3$H-hypoxanthine and for 24 hour total duration (i.e., no delay in the addition of the $^3$H-hypoxanthine). As before, the incorporated radioactivity was used as a-measure for parasite growth.

Selected compounds were also tested against drug-resistant parasites. The method was the same as above except for the following modifications. The parasite used was the chloroquine-resistant strain, K1, maintained essentially according to Desjardins, et al. (supra, 1979). The culture medium was RPMI-1640 containing TES (Sigma; 7.64 $gL^{-1}$), glucose (BDH; 1.67 $gL^{-1}$), $NaHCO_3$ (BDH; 1.94 $gL^{-1}$), and gentamycin (Nicholas; 30 $mgL^{-1}$) supplemented with 10% human serum (A RH+). Parasites were subinoculated every 3–4 days with initial conditions of 1% parasitemia and 2.5% hematocrit. For the testing, small aliquots of test material were dissolved in 20 μl EtOH and RPMI 1640 to give solutions of 1 or 10 mg $ml^{-1}$. Each was applied in a series of twelve, 7-fold dilutions (final counts ranging from 50 to $1.19\times10^{-3}$ μg $ml^{-1}$). Chloroquine diphosphate (Sigma) was used in the same experiments as a reference and also in twelve, 4-fold dilutions (final concentrations $2\times10^{-5}–1.19\times10^{-12}$M). Each compound was tested in duplicate.

Testing was performed in vitro based upon the method of Desjardins, et al (supra, 1979), as modified by O'Neill, et al. (Planta Med., 51, 394–399, 1985) and Ekong, et al. (Biochem. Pharmacol., 40, 297–301, 1990). The parasites (50 μl initial parasitemia of 1%, hematocrit of 5%) were incubated for 24 h in microtitre plates (Nunc) in normal (not hypoxanthine-depleted) medium in the presence of 50 μl of test solution. Controls were set up in each test by preparing 12–24 wells with non-parasitized RBC's and no test solution strain), and *P. berghei* (Anka) in vitro. The results, summarized in Table 2, indicated that these compounds had antimalarial activity against all of these parasites, including the drug-resistant strain, albeit with varying potencies depending upon the particular compound and parasite strain.

TABLE 2

$IC_{50}$ values of pure naphthylisoquinoline alkaloids, obtained with *Plasmodium falciparum* (NF 54, clone A149) and *P. berghei* (Anka) in vitro. Six repeats. Maximum concentration: 50 or 5 μg ml$^{-1}$. Seven four-fold dilutions.

| Naphthylisoquinoline alkaloid | $IC_{50}$ *P. falciparum* NF54 strain (μg/ml) | $IC_{50}$ *P. falciparum*, K1 strain (μg/ml) | $IC_{50}$ *P. berghei*, Anka(μg/ml) |
|---|---|---|---|
| Dioncophylline B | 0.224 | 0.063 | 0.228 |
| Dioncopeltine A | 0.021 | 0.330 | 0.038 |
| Dioncophylline A | 1.443 | 0.860 | 0.961 |
| Dioncophylline C | 0.005 | N.D. | 0.015 |
| Dioncolactone A | 1.337 | N.D. | 0.598 |
| N-methyl-dioncophylline A | 13.637 | 5.749 | 9.207 |
| Ancistrobrevine D | 12.222 | 10.440 | 6.069 |
| Ancistrocladine | 18.353 | 25.350 | >50 |
| Michellamine A | 46.957 | N.D. | >50 |
| Michellamine B | 20.185 | N.D. | >50 |
| N-methyl-dioncophylline A (atropisomers) | 17.411 | N.D. | N.D. |
| 8-O-methyl-5'-O-demethyl-7-epi-dioncophylline A | 1.584 | N.D. | 4.580 |
| Dioncophylline A/4'-O-demethyl-dioncophylline A | 0.411 | N.D. | 0.438 |
| Dioncophylleine A | 21.295 | N.D. | N.D. |
| (±)-dioncophyllacine A | 17.571 | N.D. | N.D. |
| Hamatine/ancistrocladine | 2.001 | N.D. | N.D. |
| Hamatine/ancistrobrevine B | 2.004 | N.D. | N.D. |
| Ancistrobrevine A | 19.336 | N.D. | N.D. |
| Ancistrobrevine D/6-O-demethyl-ancistrobrevine A | 2.070 | N.D. | N.D. |
| 6-O-demethyl-8-O-methyl-7-epi-ancistrobrevine C | 10.326 | N.D. | N.D. |
| Hamatine | 3.338 | N.D. | 5.565 |
| 7-epi-dioncophylline A | 0.190 | N.D. | N.D. |
| N-formyl-ancistrocladine | 8.129 | N.D. | N.D. |
| N-methyl-ancistrocladine | 0.491 | N.D. | N.D. |
| 6-deoxy-N-methyl-ancistrocladine | 10.079 | N.D. | N.D. |
| N-formyl-O,O-dimethyl-dioncophylline C | >50 | N.D. | N.D. |
| N-formyl-dioncophylline C | 3.132 | N.D. | N.D. |

N.D. = not determined and 12–24 wells with parasitized RBC's and no test compound. Thereafter, 5 μl all of $^3$H-hypoxanthine (Amersham) were added (0.2 μCi well$^{-1}$), and the parasites incubated for a further period of 18 h. Each well was harvested with a Cell Harvester (Skatron). Glass fibre filters were dried briefly. Radioactivity was measured by liquid scintillation counting in Ecoscint (National Diagnostics).

The results obtained as cpm were expressed as percentages of incorporation of growth inhibition. The dose-related part of the sigmoidal curves obtained were linearized by regression analysis with the aid of software developed by S. Grant (I.SHTM) and used to calculate the $IC_{50}$ values.

Using the above methods, the aforementioned naphthylisoquinoline alkaloids (Table 1) were tested against *P. falciparum* (NF54 strain, clone A149), *P. falciparum* (K1

The naphthylisoquinoline compounds and derivatives of the present invention can also be shown to have in vivo antimalarial activity. For example, dioncopeltine A and dioncophylline B (Table 1) were tested in vivo as follows:

Outbred, female, six-week-old OF1 mice (six mice per group treated and nontreated [control]) were inoculated intraperitoneally on day 0 with $10^6$ *P. berghei* (Anka strain) blood forms. Two hours later, they were administered orally 50 mg/kg of dioncopeltine A or dioncophylline B. A second, third, and fourth treatment (50 mg/kg each) was given after 24, 48 and 72 h, respectively (days 1, 2, and 3). A microscopic examination of the relative extent of the in vivo parasitemia, performed from blood smears taken at day 4, revealed a marked inhibition of the development of *P. berghei* blood forms. The parasitemia (%) in the control (not drug-treated) group was 3.50 (range 3.02–3.97; N=6). In the dioncopeltine A treated group, the parasitemia was 0.03 (range 0.01–0.06; N=6); in the dioncophylline B treated group, the parasitemia was 1.86 L (range 0.66–3.07; N=6). In neither of the treated groups were any signs of toxicity or other side effects observed.

Dioncophylline C (Table 1), was selected for a more detailed demonstration of the in vivo antimalarial activity of a representative naphthylisoquinoline compound. The in vivo antimalarial testing was performed as described above, except that more doses and different treatment schedules were employed, as described in Tables 3 and 4.

TABLE 3

Parasitemia of OF1 mice treated with dioncophylline C. Four consecutive days (days 0, 1, 2, and 3) of oral treatment with a series of doses ranging from 3.125 to 100 mg $kg^{-1}d^{-1}$, starting 2 hours after inoculation with *Plasmodium berghei* (Anka strain, $10^6$ parasites, i.p. administered). Six mice per group. Average values, and lower and upper limits of the 95% confidence intervals.

| Applied dose of dioncophylline C (mg $kg^{-1}d^{-1}$) | Parasitemia (%) at day 4 | Parasitemia (%) at day 10 |
|---|---|---|
| 0 | 5.66 (3.81 – 7.51) (n = 6) | 23.95 (0.00 – 67.15) (n = 3) |
| 3.125 | 5.36 (3.96 – 6.75) (n = 6) | — (6†/6) |
| 6.25 | 4.42 (2.77 – 6.06) (n = 6) | — (6†/6) |
| 12.5 | 3.36 (2.35 – 4.37) (n = 6) | 26.91 (0.00 – 60.36) (n = 3, 3†/6) |
| 25 | 0.62 (0.00 – 1.34) (n = 6) | 29.82 (11.20 – 48.43) (n = 5, 1†/6) |
| 50 | 0.00 (0.00 – 0.00) (n = 6) | 0.00 (0.00 – 0.00) (n = 6) |
| 100 | 0.00 (0.00 – 0.00) (n = 6) | 0.00 (0.00 – 0.00) (n = 5*) |

†= animal(s) dead
*One OF1 was devoured by the others
Note:
At day 85, 5/5 of the OF1 treated with 100 mg $kg^{-1}d^{-1}$ and 6/6 of the OF1 treated with 50 mg $kg^{-1}d^{-1}$ dioncophylline C were still alive and looked absolutely normal.

TABLE 4

Parasitemia of OF1 mice treated with dioncophylline C. One, 2, 3 or 4 consecutive days of oral treatment (from day 0 on) with 50 mg $kg^{-1}d^{-1}$, starting 2 hours after inoculation with *Plasmodium berghei* (Anka strain, $10^6$ parasites, i.p. administered). Six mice per group. Average values, and lower and upper limits of the 95% confidence intervals.

| Days of treatment with 50 mg dioncophylline C ($kg^{-1}d^{-1}$) | Parasitemia (%) at day 4 | Parasitemia (%) at day 10 |
|---|---|---|
| 0 | 5.66 (3.81 – 7.51) (n = 6) | 23.95 (0.00 – 67.15) (n = 3) |
| 1 | 0.02 (0.00 – 0.05) (n = 6) | 7.87 (0.00 – 23.92) (n = 4) |
| 2 | 0.01 (0.00 – 0.02) (n = 6) | 0.41 (0.00 – 1.38) (n = 5) (2 OF1 neg) |
| 3 | 0.00 (0.00 – 0.00) (n = 6) | 0.003 (0.000 – 0.012) (n = 6) (5 OF1 neg) |
| 4 | 0.00 (0.00 – 0.00) (n = 6) | 0.00 (0.00 – 0.00) (n = 6) (6 OF1 neg) |

Note:
At day 85, 6/6 of the OF1 treated for 4 days, 4/6 of the OF1 treated for 3 days and 1/6 of the OF1 treated for 2 days with dioncophylline C were still alive and looked absolutely normal.

Table 3 shows that four consecutive daily oral administrations of 12.5–100 mg $kg^{-1}d^{-1}$ of the naphthylisoquinoline alkaloid produced striking in vivo antimalarial activity. The higher doses (e.g., 50 and 100 mg $kg^{-1}d^{-1}$) produced apparent cures, with no observed evidence of toxicity at the end of the 85 day observation period. Loss of body weight was observed only in mice (5/6) treated with 100 mg $kg^{-1}d^{-1}$, after the fourth treatment. One out of the 6 mice had motor problems with the hind legs. However, both phenomena were transitory, and all mice fully recovered during the observation period.

Based upon the results summarized in Table 3, a study was performed using 1, 2, 3, or 4 consecutive days of oral administration of 50 mg $kg^{-1}d^{-1}$ of the naphthylisoquinoline alkaloid. The results, summarized in Table 4, show that the naphthylisoquinoline compound could cure malaria in this in vivo animal model. In this representative study, oral treatment with 4×50 mg $kg^{-1}d^{1}$ dioncophylline C completely and permanently inhibited the development of erythrocytic forms of *P. berghei* while causing no observed indications of any toxicity.

Example 3

This example illustrates various possible pharmaceutical compositions which include the antimalarial compounds of the present invention.

The compounds of the present invention may be made into pharmaceutical compositions by combination with appropriate pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective routes of administration.

The compounds can be used singularly alone, in combination with each other, or in combination with other antimalarial agents. When mammals infected with malaria parasites are being treated, at least one compound of the present invention can be co-administered with chloroquine or other antimalarial agent(s) such as mefloquine, halofantrine, artemisinin, artemether, pyrimethamine, or quinine.

The following methods and excipients are merely exemplary and are in no way limiting:

In pharmaceutical dosage forms, the compounds of the present invention may be used in the form of their pharmaceutically acceptable salts and also may be used alone or in appropriate association, as well as in combination, with other pharmaceutically active compounds.

In the case of oral preparations, the compounds of the present invention may be used alone or in combination with appropriate additives to make tablets, powders, granules, or capsules, e.g., with conventional additives such as lactose, mannitol, corn starch, or potato starch; with binders such as crystalline cellulose, cellulose derivatives, acacia, corn starch, or gelatins; with disintegrators such as corn starch, potato starch, or sodium carboxymethylcellulose; with lubricants such as talc or magnesium stearate; and, if desired, with diluents, buffering agents, moistening agents, preservatives, and flavoring agents.

The compounds of the present invention may be formulated into preparations for injections by dissolving, suspending, or emulsifying them in an aqueous or nonaqueous solvent, such as vegetable or other similar oils, synthetic aliphatic acid glycerides, esters of higher aliphatic acids, or propylene glycol; and, if desired, with conventional additives such as solubilizers, isotonic agents, suspending agents, emulsifying agents, stabilizers and preservatives.

The compounds of the present invention can be utilized in aerosol formulation to be administered via inhalation. The compounds of the present invention can be formulated into pressurized acceptable propellants such as dichlorodifluoromethane, propane, nitrogen, and the like.

Furthermore, the compounds of the present invention may be made into suppositories by mixing with a variety of bases such as emulsifying bases or water-soluble bases. The compounds of the present invention can be administered rectally via a suppository. The suppository can include vehicles such as cocoa butter, carbowaxes, and polyethylene glycols, which melt at body temperature, yet are solid at room temperature.

Unit dosage forms for oral or rectal administration such as syrups, elixirs, and suspensions may be provided wherein each dosage unit, e.g., teaspoonful, tablespoonful, tablet, or suppository contains a predetermined amount of the composition containing at least one compound of the present invention; similarly, unit dosage forms for injection or intravenous administration may comprise a naphthylisoquinoline alkaloid composition as a solution in sterile water, normal saline, or other pharmaceutically acceptable carrier.

The term "unit dosage form" as used herein refers to physically discrete units suitable as unitary dosages for human and animal subjects, each unit containing a predetermined quantity of at least one compound of the present invention calculated in an amount sufficient to produce the desired effect in association with a pharmaceutically acceptable, diluent, carrier, or vehicle. The specifications for the novel unit dosage forms of the present invention depend on the particular compound employed and the effect to be achieved, as well as the pharmacodynamics associated with each compound in the particular host.

The pharmaceutically acceptable excipients, for example, vehicles, adjuvants, carriers, or diluents, are readily available to the public.

One skilled in the art can determine easily the appropriate method of administration for the precise formulation of the composition being used. Any necessary adjustments in dose can be made readily to meet the nature or severity of the infection and adjusted accordingly by the skilled practitioner.

Example 4

This example illustrates various possible uses of the antimalarial naphthylisoquinoline alkaloids and derivatives of the present invention in the treatment or prevention of malarial infections.

An antimalarial effective amount of at least one compound of the present invention can be administered to a mammal, particularly a human, to treat or prevent malarial infections. An antimalarial effective amount is defined as that amount of compound required to be administered to an individual mammal to achieve an antimalarial effective blood and/or tissue level to inhibit the parasite. The antimalarial effective blood level might be chosen, for example, to inhibit Plasmodia parasites in an in vitro screening assay. An example of such a level would be 0.001–100 µg/ml, depending upon the particular compound selected for use (e.g, from Example 2). Alternatively, the antimalarial effective blood level can be defined as that concentration which demonstrably inhibits the presence, viability, or reproduction of the parasite in the recipient mammalus blood, or which renders the mammal asymptomatic to the particular malarial infection. Since a target antimalarial effective blood level is used as the preferred endpoint for dosing, the actual dose and schedule for drug administration for each particular recipient mammal will vary depending upon interindividual differences in the pharmacokinetics, drug disposition, and metabolism of the particular compound selected for use. Moreover, the dose may vary when the compounds are used prophylactically or when used in combination with other drugs.

Such dosage amounts can be readily ascertained without undue burden and experimentation by those skilled in the art. As an example of an antimalarial effective amount, the daily dosage for a particular recipient mammal can range from about between 0.01 mg/kg body weight to 100 mg/kg body weight, depending upon the particular compound selected for use.

All of the references cited herein, including patents, patent applications, literature publications, and the like, are hereby incorporated in their entireties by reference.

While this invention has been described with an emphasis upon preferred embodiments, it will be obvious to those, of ordinary skill in the art that variations of the preferred products and methods may be used and that it is intended that the invention may be practiced otherwise than as specifically described herein. Accordingly, this invention includes all modifications encompassed within the spirit and scope of the invention as defined by the following claims.

What is claimed is:

1. A pharmaceutical composition consisting essentially of at least one pharmaceutically acceptable carrier and an antimalarially effective amount of at least one compound selected from the group consisting of dioncophylline B, dioncopeltine A, dioncophylline A, dioncophylline C, ancistrobrevine D, ancistrocladine, N-methyl-dioncophylline A and the atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and pharmacologically acceptable salts thereof, optionally in combination with an antimalarially effective amount of at least one additional antimalarial compound selected from the group consisting of chloroquine, mefloquine, halofantrine, artemisinin, artemether, pyrimethamine, and quinine.

2. The pharmaceutical composition of claim 1, wherein said compound is selected from the group consisting of dioncophylline B, dioncopeltine A, 7-epi-dioncophylline A, N-methyl-ancistrocladine, and dioncophylline C, and pharmacologically acceptable salts thereof.

3. The pharmaceutical composition of claim 1, wherein said compound is dioncophylline C or a pharmacologically acceptable salt thereof.

4. A pharmaceutical composition which comprises a pharmaceutically acceptable carrier and an antimalarially effective amount of at least one compound selected from the group consisting of derivatives of dioncophylline B, dioncopeltine A, dioncophylline A, dioncophylline C, ancistrobrevine D, ancistrocladine, N-methyl-dioncophylline A and the atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein one or more phenolic hydroxyl group(s) is an ester, sulfonate ester, or ether group; one or more secondary amine site(s) is an amide, tertiary amine, or alkyl quaternary ammonium salt; and/or one or more tertiary amine site(s) is a secondary amine, and pharmacologically acceptable salts thereof.

5. The pharmaceutical composition of claim 4, wherein said compound is selected from the group consisting of derivatives of dioncophylline B, dioncopeltine A, 7-epi-dioncophylline A, N-methyl-ancistrocladine, and dioncophylline C, and pharmacologically acceptable salts thereof.

6. The pharmaceutical composition of claim 4, wherein said compound is a derivative of dioncophylline C or a pharmacologically acceptable salt thereof.

7. A method of treating or preventing a malarial infection which comprises administering to a mammal in need thereof an antimalarially effective amount of at least one compound selected from the group consisting of dioncophylline B, dioncopeltine A, dioncophylline A, dioncophylline C, ancistrobrevine D, ancistrocladine, N-methyl-dioncophylline A and atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and pharmacologically acceptable salts thereof.

8. The method of claim 7, wherein said compound is selected from the group consisting of dioncophylline B, dioncopeltine A, 7-epi-dioncophylline A, N-methyl-ancistrocladine, and dioncophylline C, and pharmacologically acceptable salts thereof.

9. The method of claim 7, wherein said compound is dioncophylline C or a pharmacologically acceptable salt thereof.

10. A method of treating or preventing a malarial infection which comprises administering to a mammal in need thereof an antimalarially effective amount of at least one compound selected from the group consisting of derivatives of dioncophylline B, dioncopeltine A, dioncophylline A, dioncophylline C, ancistrobrevine D, ancistrocladine, N-methyl-dioncophylline A and the atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein one or more phenolic hydroxyl group(s) is an ester, sulfonate ester, or ether group; one or more secondary amine site(s) is an amide, tertiary amine, or alkyl quaternary ammonium salt; and/or one or more tertiary amine site(s) is a secondary amine, and pharmacologically acceptable salts thereof.

11. The method of claim 10, wherein said compound is selected from the group consisting of derivatives of dioncophylline B, dioncopeltine A, 7-epi-dioncophylline A, N-methyl-ancistrocladine, and dioncophylline C, and pharmacologically acceptable salts thereof.

12. The method of claim 10, wherein said compound is a derivative of dioncophylline C or a pharmacologically acceptable salt thereof.

13. A method of inhibiting the growth of a malarial parasite comprising contacting said malarial parasite with a malarial growth inhibiting effective amount of at least one compound selected from the group consisting of dioncophylline B, dioncopeltine A, dioncophylline A, dioncophylline C, ancistrobrevine D, ancistrocladine, N-methyl-dioncophylline A and the atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, and pharmacologically acceptable salts thereof.

14. The method of claim 13, wherein said compound is selected from the group consisting of dioncophylline B, dioncopeltine A, 7-epi-dioncophylline A, N-methyl-ancistrocladine, and dioncophylline C, and pharmacologically acceptable salts thereof.

15. The method of claim 13, wherein said compound is dioncophylline C or a pharmacologically acceptable salt thereof.

16. A method of inhibiting the growth of a malarial parasite comprising contacting said malarial parasite with a malarial growth inhibiting effective amount of at least one compound selected from the group consisting of derivatives of dioncophylline B, dioncopeltine A, dioncophylline A, dioncophylline C, ancistrobrevine D, ancistrocladine, N-methyl-dioncophylline A and the atropisomer thereof, dioncophylleine A, (±)-dioncophyllacine A, hamatine, ancistrobrevine B, ancistrobrevine A, 6-O-demethyl-ancistrobrevine A, ancistrobarterine A, 7-epi-dioncophylline A, N-formyl-ancistrocladine, N-methyl-ancistrocladine, 6-deoxy-N-methyl-ancistrocladine, N-formyl-O,O-dimethyl-dioncophylline C, N-formyl-dioncophylline C, N-formyl-8-O-benzyl-dioncophylline C, N-formyl-8-O-methyl-dioncophylline C, N-formyl-8-O-pivaloyl-dioncophylline C, N-formyl-8-O-acetyl-dioncophylline C, N-formyl-8-O-benzoyl-dioncophylline C, and 8-O-methyl-dioncophylline C, wherein one or more phenolic hydroxyl group(s) is an ester, sulfonate ester, or ether group; one or more secondary amine site(s) is an amide, tertiary amine, or alkyl quaternary ammonium salt; and/or one or more tertiary amine site(s) is a secondary amine, and pharmacologically acceptable salts thereof.

17. The method of claim 16, wherein said compound is selected from the group consisting of derivatives of dioncophylline B, dioncopeltine A, 7-epi-dioncophylline A, N-methyl-ancistrocladine, and dioncophylline C, and pharmacologically acceptable salts thereof.

18. The method of claim 16, wherein said compound is a derivative of dioncophylline C or a pharmacologically acceptable salt thereof.

* * * * *